United States Patent
Gralla et al.

(10) Patent No.: US 7,960,593 B2
(45) Date of Patent: Jun. 14, 2011

(54) PROCESS FOR PREPARATION OF MENTHOL BY HYDROGENATION OF ISOPULEGOL

(75) Inventors: Gabriele Gralla, Mannheim (DE); Gunnar Heydrich, Limburgerhof (DE); Eike Johannes Bergner, Hirschberg (DE); Klaus Ebel, Lampertheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/670,328

(22) PCT Filed: Jul. 16, 2008

(86) PCT No.: PCT/EP2008/059277
§ 371 (c)(1),
(2), (4) Date: Jan. 22, 2010

(87) PCT Pub. No.: WO2009/013192
PCT Pub. Date: Jan. 29, 2009

(65) Prior Publication Data
US 2010/0191021 A1    Jul. 29, 2010

(30) Foreign Application Priority Data
Jul. 23, 2007  (EP) ..................... 07112951

(51) Int. Cl.
*C07C 29/00*  (2006.01)
*C07C 35/12*  (2006.01)

(52) U.S. Cl. ........................................ 568/830

(58) Field of Classification Search ............ 568/830
See application file for complete search history.

(56) References Cited

U.S. PATENT DOCUMENTS

| 5,037,793 | A  | 8/1991 | Toussaint et al. |
| 5,530,127 | A  | 6/1996 | Reif et al. |
| 7,868,211 | B2 | 1/2011 | Rauls et al. |
| 2006/0167322 | A1 | 7/2006 | Kuhn et al. |
| 2008/0167504 | A1 | 7/2008 | Friedrich et al. |
| 2008/0214877 | A1 | 9/2008 | Rauls et al. |
| 2010/0010253 | A1 | 1/2010 | Heydrich et al. |
| 2010/0016642 | A1 | 1/2010 | Heydrich et al. |
| 2010/0185024 | A1 | 7/2010 | Rauls et al. |
| 2010/0193348 | A1 | 8/2010 | Heydrich et al. |

FOREIGN PATENT DOCUMENTS

| DE | 577036 C | 5/1933 |
| DE | 10239274 A1 | 3/2004 |
| EP | 0394842 A1 | 10/1990 |
| EP | 0696572 A1 | 2/1996 |
| EP | 1053974 A1 | 11/2000 |
| EP | 1532091 A1 | 5/2005 |
| GB | 1503723 A | 3/1978 |
| WO | WO-2006/092433 A1 | 9/2006 |

OTHER PUBLICATIONS

Dudley Sully, B., et al., "The Optical Rotation of Citronellel," P.& E.O.R., vol. 59, pp. 365-366 (1968).
Pickard, R. H, et al., "The Alcohols of the Hydroaromatic and Terpene Series, Part III. isoPulegol," Journal of the Chemical Society, Transactions vol. 117, pp. 1248-1263 (1920).

*Primary Examiner* — Sikarl A Witherspoon
(74) *Attorney, Agent, or Firm* — Connolly Bove Lodge & Hutz LLP

(57) ABSTRACT

The present invention relates to a process for preparing racemic or optically active menthol by catalytically hydrogenating racemic or optically active isopulegol in the presence of hydrogen and catalysts which comprise nickel-, copper-, zirconium- and molybdenum-containing compounds. The present invention relates specifically to a corresponding process far continuously catalytically hydrogenating L-isopulegol to L-menthol.

13 Claims, No Drawings

PROCESS FOR PREPARATION OF MENTHOL BY HYDROGENATION OF ISOPULEGOL

RELATED APPLICATIONS

This application is a national stage application (under 35 U.S.C. §371) of PCT/EP2008/059277, filed Jul. 16, 2008, which claims benefit of European Application No. 07112951.4, filed Jul. 23, 2007.

The present invention relates to a process for preparing racemic or optically active menthol by catalytically hydrogenating racemic or optically active isopulegol in the presence of hydrogen and catalysts which comprise nickel-, copper-, zirconium- and molybdenum-containing compounds. The present invention relates specifically to a corresponding process for continuously catalytically hydrogenating L-isopulegol to L-menthol.

Menthol, especially the naturally occurring L-menthol, owing to its minty aroma and its cooling and refreshing properties, is one of the globally most important aroma chemicals and is used to a considerable degree to flavor consumable goods of all kinds.

L-menthol can be obtained from natural sources, for example by crystallization from peppermint oil, or else by synthetic processes. According to the prior art, menthol can be obtained, for example, by dearomatizing hydrogenation of thymol, in which case it is typically obtained in the form of a mixture of the diastereomers of menthol, neomenthol, isomenthol and neoisomenthol, from which it has to be isolated by further process steps.

DE 577 036 discloses a process for preparing synthetic menthol by hydrogenating thymol. Nickel, nickel/copper and cobalt catalysts are described as suitable catalysts.

Specific nickel catalysts have also been used for catalytic hydrogenation of piperitol to menthol, as described in GB 1,503,723.

EP 1 532 091 discloses a process for preparing racemic menthol by catalytically hydrogenating isopulegol, which was used in the form of a diastereomer mixture of 70.1% isopulegol, 18.1% neoIsopulegol, 6.8% isoisopulegol and 2.6% neoisoisopulegol. The catalyst used was iron- and chromium-doped Raney nickel. Menthol was obtained in the form of a mixture of the possible diastereomers, which consisted to an extent of 61.4% of menthol and to an extent of 35.6% of the further diastereomers of menthol.

A further route to menthol is that of processes for diastereoselective cyclization of citronellal to isopulegol, as described, for example, in WO 2006/092433. The isopulegol thus obtained can then be hydrogenated to menthol in a further step.

R. H. Pickard et al. describe, in J. Chem. Soc. 1920, 1248 to 1263, the preparation of L-menthol by catalytically hydrogenating L-isopulegol in the presence of colloidal palladium.

B. Dudley Sully et al. describe, in P.& E.O.R. 1068, 235 to 366, the preparation of L-menthol by hydrogenating L-isopulegol in the presence of Raney nickel at a temperature of 120° C.

Die EP 1 053 974 discloses a process for catalytically hydrogenating isopulegol to menthol in the presence of a catalyst of 5% palladium on carbon at a hydrogen pressure of 5 bar.

EP 0 394 842 relates to catalysts for the hydrogenation of aliphatic unsaturated compounds, which comprise nickel and copper and are characterized by a content of from 20% to 75% by weight of nickel oxide, from 10 to 75% by weight of zirconium dioxide and from 5 to 50% by weight of copper oxide, based in each case on the oxidic unreduced catalyst. Examples of substrates specified are: butyne-2-diol-1,4, butene-2-diol-1,4 and 2-ethylhexene-2-al.

Proceeding from this prior art, it was an object of the present invention to provide a process which enables the preparation of essentially diastereomerically pure menthol by hydrogenation of essentially diastereomerically pure isopulegol. The process should be performable on the industrial scale in an easily manageable manner in terms of process technology and should lead to the desired product in a high chemical yield using inexpensive catalysts or reagents. The formation of diastereomers of menthol should be avoided as far as possible. Furthermore, the formation of an undesired menthone or isomenthone and neoisomenthol should be very substantially prevented.

The object is achieved in accordance with the invention by provision of a process for preparing racemic or optically active menthol of the formula (I)

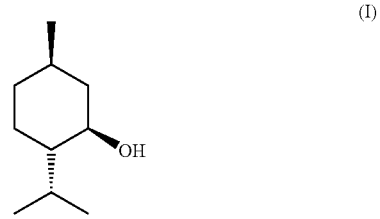

by catalytically hydrogenating racemic or optically active isopulegol of the formula (II)

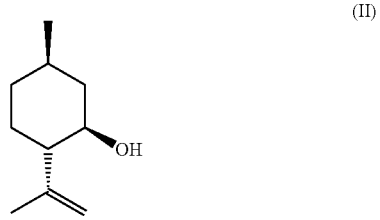

in the presence of hydrogen and a catalyst comprising
from 30 to 70% by weight of oxygen compounds of nickel, calculated as NiO,
from 15 to 45% by weight of oxygen compounds of zirconium, calculated as $ZrO_2$,
from 5 to 30% by weight of oxygen compounds of copper, calculated as CuO and
from 0.1 to 10% by weight of oxygen compounds of molybdenum, calculated as $MoO_3$,
where the figures in % by weight are based on the dry unreduced catalyst.

A suitable starting material for performing the process according to the invention is racemic or optically active isopulegol of the formula (II), although it is possible in principle to use isopulegol of any purity. However, the process according to the invention is suitable preferably for conversion of isopulegol of high purity, i.e. of isopulegol having a purity of 80% by weight or higher, preferably of 90% by weight or higher. Especially suitable as a starting material for performing the process according to the invention is that isopulegol having a chemical purity of 97% by weight or higher, preferably of from 98 to 100% by weight, more preferably from 98.5 to 99.9% by weight, most preferably of from at least 99 to 99.9% by weight. The term "chemical purity" also comprises the diastereomeric purity of the isopulegol used with respect to the diastereomers of neoisoisopulegol of the formula (III), neoIsopulegol of the formula (IV) and isoisopulegol of the formula (V).

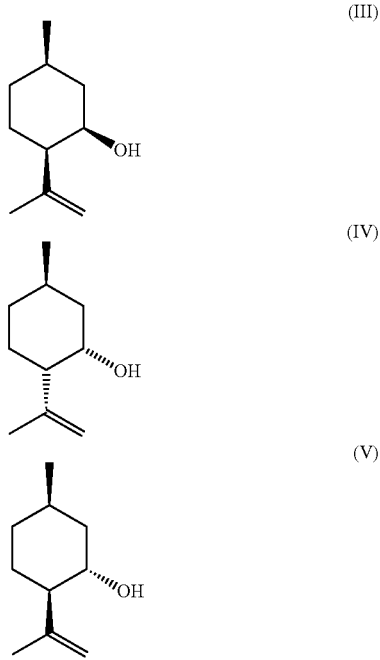

Accordingly, isopulegol which is particularly preferred as a starting material for performing the process according to the invention has a diastereomeric purity as described above of 97% by weight or higher, preferably from 98 to 100% by weight, more preferably from 98.5 to 99.9% by weight and most preferably from at least 99 to 99.9% by weight. The formulae specified may, like all formulae depicted in the context of the present invention, each represent both enantiomers (of mixtures thereof) and serve to illustrate the relative configuration of the stereogenic centers.

According to the invention, isopulegol can be used, in racemic or nonracemic, i.e. optically active, form. In the case of use of racemic isopulegol of the formula (II), in accordance with the invention, racemic menthol of the formula (I) is obtained. In the case of use of optically active isopulegol of the formula (II), optically active menthol of the formula (I) is correspondingly obtained. When isopulegol is used in optically active form, preference is given in accordance with the invention to those mixtures which comprise predominantly the L-isopulegol enantiomer, as reproduced by way of example in formula (II) in terms of its absolute configuration.

Preference is given in accordance with the invention to using isopulegol, i.e. D- or preferably L-isopulegol, with an enantiomeric excess (ee) of 80% ee or higher, preferably of 85 or better of 90% as or higher, more preferably from 95 to 100% ee, even more preferably from 96 to 99.9% ee, further preferably from 97 to 99.8% ee, even more preferably from 98 to 99.7% ee and especially preferably from 98.5 to 99.6% ee. Proceeding from L-isopulegol in optically active form, L-menthol in optically active form is obtained in the inventive manner.

The process according to the invention is performed in the presence of hydrogen and in the presence of a heterogeneous catalyst, the heterogeneous catalyst to be used comprising from 30 to 70% by weight, preferably from 40 to 60% by weight of oxygen compounds of nickel, calculated as NiO, from 15 to 45% by weight, preferably from 20 to 40% by weight, of oxygen compounds of zirconium, calculated as $ZrO_2$, from 5 to 30% by weight, preferably from 10 to 25% by weight, of oxygen compounds of copper, calculated as CuO and from 0.1 to 10% by weight, preferably from 0.5 to 5% by weight of oxygen compounds of molybdenum, calculated as $MoO_3$, if appropriate as well as further components in an amount of from 0 to 10% by weight, preferably from 0 to 5% by weight, for example graphite. These data in % by weight are based on the dry unreduced catalyst.

Since the concentration data are each—unless stated otherwise—based on the catalytically active material of the catalyst, the catalytically active material of the catalyst is defined hereinafter as the sum of the masses of the catalytically active zirconium, nickel, copper and molybdenum constituents in the catalyst, calculated in each case, as $ZrO_2$, NiO, CuO and $MoO_3$, respectively, after the last heat treatment thereof and before the reduction thereof with hydrogen.

In a preferred embodiment, the process according to the invention is performed by using those catalysts comprising
  from 45 to 55% by weight of oxygen compounds of nickel, calculated as NiO,
  from 25 to 35% by weight of oxygen compounds of zirconium, calculated as $ZrO_2$,
  from 5 to 20% by weight of oxygen compounds of copper, calculated as CuO,
  from 1 to 3% by weight of oxygen compounds of molybdenum, calculated as $MoO_3$ and
  from 0 to 5% by weight of further components,
where the figures in % by weight add up to 100% by weight and are based on the dry unreduced catalyst. Especially preferred in accordance with the invention are those catalysts which consist of the aforementioned components in the proportions by weight which have likewise been specified.

A catalyst which is especially preferred for use in the process according to the invention consists to an extent of from 49 to 53% by weight of NiO, to an extent of from 15 to 19% by weight of CuO, to an extent of from 28 to 32% by weight of $ZrO_2$ and to an extent of from 1 to 2% by weight of $MoO_3$, and if appropriate, to an extent of from 0 to 3% by weight of further components, for example graphite, the proportions by weight of the individual components selected in each case being based on the dry unreduced catalyst and adding up to 100% by weight. Such catalysts are known and can be prepared, for example, as described in EP 0 696 572.

The catalysts usable in accordance with the invention can be prepared, for example, by using precipitation methods. For example, they can be obtained by a coprecipitation of the nickel and copper components from an aqueous salt solution comprising these elements by means of mineral bases in the presence of a slurry of a sparingly soluble, oxygen-containing zirconium compound, and subsequent washing, drying and calcination of the resulting precipitate. The sparingly soluble oxygen-containing zirconium compounds used may, for example, be zirconium dioxide, zirconium oxide hydrate, and zirconium phosphates, borates and silicates. The slurries of the sparingly soluble zirconium compounds can be prepared by suspending fine powders of these compounds in water with vigorous stirring. These slurries are advantageously obtained by precipitating the sparingly soluble zirconium compounds from aqueous zirconium salt solutions by means of mineral bases.

Preference is given to preparing the catalysts usable in accordance with the invention by means of a coprecipitation of all of their components. To this end, an aqueous salt solution comprising the catalyst components is appropriately admixed under hot conditions and with stirring with an aqueous mineral base, especially an alkali metal base—for example sodium carbonate, sodium hydroxide, potassium carbonate or potassium hydroxide—until the precipitation is complete. The type of salts used is generally uncritical—since the principle factor in this procedure is the water-solubility of the salts, one criterion is their good water solubility, which is required to prepare these comparatively highly concentrated salt solutions. It is considered to be obvious that, in the selection of the salts of the individual components, of course only salts with those. anions which do not lead to disruption, whether by causing undesired precipitation or by complicating or preventing the precipitation by complex formation, are selected.

Catalysts which are usable in accordance with the invention and have particularly advantageous properties are obtainable by precipitating a portion of the zirconium component of the catalyst, appropriately from an aqueous zirconium salt solution, separately in a precipitation apparatus by adding aqueous mineral bases. The remaining portion of the zirconium component of the catalyst can then be precipitated onto the thus obtained, preferably freshly precipitated zirconium oxide hydrate, together with the other catalytically active components in a coprecipitation, as described above. It is generally found to be particularly appropriate to preliminarily precipitate from 10 to 80% by weight, preferably from 30 to 70% by weight and especially from 40 to 60% by weight of the total amount of zirconium of the catalytically active material.

The precipitates obtained in these precipitation reactions are generally chemically inhomogeneous and consist, inter alia, of mixtures of the oxides, oxide hydrates, hydroxides, carbonates and insoluble and basic salts of the metals mentioned. It may be found to be favorable for the filterability of the precipitates if they are aged, i.e. if they are left alone for a certain time after the precipitation, if appropriate under hot conditions or while passing air through.

The precipitates obtained by these precipitation processes can be processed further as usual to give the catalysts usable in accordance with the invention. After washing, they are generally dried at from 80 to 200° C., preferably at from 100 to 150° C., and then calcined. The calcination is performed generally at temperatures between 300 and 800° C., preferably at from 400 to 600° C., especially at from 450 to 550° C.

After calcination, the is appropriately conditioned, whether by adjusting it to a particular particle size by grinding or by grinding and then mixing it with shaping assistants such as graphite or stearic acid, pressing to pellets by means of a tableting press and heat treating. In this case, the temperatures correspond generally to the temperatures in the calcination.

The catalysts prepared in this way comprise the catalytically active metals in the form of a mixture of their oxygen compounds, i.e. more particularly as oxides and mixed oxides.

The catalysts prepared in this way can be stored and used as such. Before they are used as catalysts in the process according to the invention, they are typically prereduced. However, they can also be used without prereduction, in which case they are reduced by the hydrogen present in the reactor under the conditions of the inventive hydrogenation. For prereduction, the catalysts are generally exposed to a nitrogen-hydrogen atmosphere first at from 150 to 200° C. over a period of from 12 to 20 hours, and then treated in a hydrogen atmosphere at from 200 to 300° C. for an other up to approx. 24 hours. This, prereduction typically reduces a portion of the oxygen-containing metal compounds present in the catalysts to the corresponding metals, such that they are present in the active form of the catalyst together with the different kinds of oxygen compounds.

In general, the inventive catalysts are preferably used in the form of unsupported catalysts. The term "unsupported catalyst" refers to a catalyst which, in contrast to a supported catalyst, consists only of catalytically active material. Unsupported catalysts can be used in such a way that the catalytically active material ground to powder is introduced into the reaction vessel, or in such a way that the catalytically active material, after grinding, mixing with shaping assistants, shaping and heat treatment, is arranged in the reactor in the form of shaped catalyst bodies—for example, in the form of spheres, cylinders, tablets, rings, spirals, extrudates and many others.

In a preferred embodiment of the hydrogenation process according to the invention, the selected heterogenous catalyst is used in the form of a fixed bed catalyst.

To perform the process according to the invention, the isopulegol starting material as described above is contacted with hydrogen and the selected catalyst. The hydrogen can be used in undiluted form, typically in a purity of about 99.9% by volume or in diluted form, i.e. In the form of mixtures with inert gases, for example nitrogen or argon. Preference is given to using hydrogen in undiluted form.

The reaction can be carried out with good success without addition of solvent or in the presence of organic solvents which are inert under the reaction conditions, for example methanol, ethanol, isopropanol, hexane, heptane, cyclohexane and many others. Preference is given to performing the reaction without addition of solvent.

The inventive hydrogenation of isopulegol can be performed at a hydrogen pressure (absolute) in the range from 1 to 200 bar, preferably from 2 or better from 3 to 200 bar, more preferably from 4 or 5 to 150 bar, more preferably from 5 to 100 bar and most preferably in the range from 5 to 50 bar. The reaction temperature selected for performance of the inventive hydrogenation is advantageously a temperature in the range from 20 to 150° C., preferably from 40 to 130° C., more preferably from 60 to 110° C. and most preferably from 70 to 100° C.

In practical terms, the procedure in the performance is generally to feed the isopulegol to be converted to the catalyst, which is typically present in a preferably externally heated fixed bed reactor, for example a tubular reactor, autoclave or tube bundle reactor, at the desired reaction temperature and the desired pressure. This involves loading the catalyst generally with from 0.1 to 1.0 kg, preferably with from 0.1 to 0.6 kg and more preferably with from 0.2 to 0.4 kg of isopulegol per kg of catalyst and per hour. It may be appropriate here to heat the isopulegol for use actually before it is fed into the reaction vessel or the reactor, specifically preferably to the reaction temperature.

The reactor can be operated either in liquid phase mode or in trickle mode, i.e. the starting materials can be passed through the reactor either from the bottom upward or from the top downward. The hydrogenation process according to the invention can be performed either batchwise or continuously. In both cases, unconverted reactant can be circulated together with the hydrogen.

The inventive hydrogenation can also be performed stepwise in a cascade of a plurality of, i.e. from 2 to generally 4, preferably 2 or 3 and especially preferably in two reactors connected in series, preferably fixed bed reactors. In this case, the main conversion of the reaction is achieved in the first reactor, typically referred to as the main reactor, under the above-described reaction conditions, and the resulting crude product is fed to a second reactor, typically referred to as the postreactor, in which the as yet unconverted starting material is converted in the inventive manner at least substantially to L-menthol. The reaction conditions can preferably be selected independently of one another within the aforementioned ranges.

The process according to the invention can be performed batchwise, semicontinuously, or fully continuously. Preference is given to performing the process continuously, especially fully continuously, the starting materials being introduced continuously into the reactor and the resulting reaction mixture or reaction product being discharged continuously from the reactor. It has additionally been found to be advantageous, owing to the position of the melting point of the inventive menthol reaction product, specifically L-menthol, to provide heating of the transport lines used.

The process according to the invention allows the preparation of menthol by catalytic hydrogenation of isopulegol, typically resulting only in a low degree of formation of undesired diastereomers of menthol. Accordingly, the process according to the invention provides, in the case of use of isopulegol of appropriate purity, menthol of the formula (I) in a chemical purity of 97% by weight or higher, preferably from 98 to 100% by weight, more preferably from 98.5 to 99.9% by weight, most preferably from at least 99 to 99.9% by weight. The term "chemical purity" also comprises the diastereomeric purity of the resulting menthol with respect to the diastereomers of neoisomenthol of the formula (VI), neomenthol of the formula (VII) and isomenthol of the formula (VIII). Accordingly, the process according to the invention in the frame preferably provides menthol with a diastereomeric purity of 97% by weight or higher, preferably from 98 to 100% by weight, more preferably from 98.5 to 99.9% by weight and most preferably from at least 99 to 99.9% by weight.

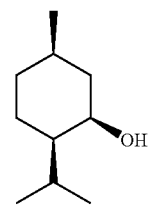

(VI)

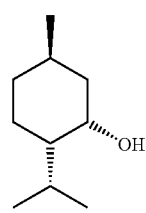

(VII)

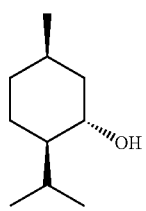

(VIII)

When isopulegol is used in optically active form, preferably in accordance with the invention those mixtures which comprise predominantly the L-isopulegol enantiomer, the inventive process product obtained is generally menthol in optically active form, preferably in the form of or (-)- L-menthol. The inventive hydrogenation proceeds generally substantially without any significant racemization of the material used. Accordingly, depending on the enantiomeric excess of the optically active isopulegol used, optically active menthol, preferably L-menthol when L-isopulegol is used, is obtained with an enantiomeric excess (ee) of 80% ee or higher, preferably of 85 or 90% ee or higher, more preferably from 95 to 100% ee, more preferably from 96 to 99.9% ee, most preferably from 97 to 99.8% ee, even more preferably from 98 to 99.7% ee and especially preferably from 98.5 to 99.6% ee.

The menthol obtained in accordance with the invention additionally features a particularly low content of the undesired by-products of menthone of the formula (IX) and isomenthone of the formula (X) and neoisomenthol of the formula (VI).

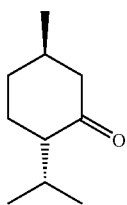

(IX)

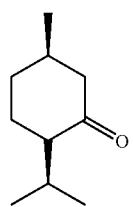

(X)

These by-products are generally obtained in the process according to the invention only in a proportion, based on the amount of menthol obtained, of up to 0.5% by weight, preferably 0.4% by weight, more preferably 0.3% by weight, especially 0.2% by weight and most preferably from 0.1 to 0% by weight.

EXAMPLES

The examples which follow serve to illustrate the invention, without restricting it in any way: Gas chromatography analyses were performed by the following method:

50 m CP-WAX, ID: 0.32 mm, FD: 1.2 µm; 80° C., 3° C./min-200° C., 10° C./min to 230° C.; $t_R$ (menthone): 26.9; $t_R$ (menthone): 28.1; $t_R$ (isopulegol): 30.7; $t_R$ (neomenthol): 31.2; $t_R$ (neoisomenthol): 32.6; $t_R$ (menthol): 32.7; $t_R$ (isomenthol): 34.1.

The isopulegol used was analyzed by gas chromatography as follows:

50 m CP-WAX, ID: 0.32 mm, FD: 1.2 µm; 80° C., 3° C./min-200° C., 15° C./min to 250° C.; $t_R$ (citronellal): 21.6; $t_R$ (isopulegol isomer): 25.4; $t_R$ (isopulegol): 25.9; $t_R$ (citronellol): 32.7.

Example 1

A hydrogenation apparatus consisting of a main reactor (MR) and a postreactor (PR) was used. The main reactor had 5 tubes, connected in series, with an internal diameter of 5 mm and a length of 1.3 m, which were filled with 61 g (127 ml) of a fixed bed catalyst comprising 50% by weight of NiO, 17% by weight of CuO, 30.5% by weight of $ZrO_2$, 1.5% by weight of $MoO_3$ and 1% by weight of graphite in the form of tablets with a diameter and a height of in each case 3 mm. The postreactor (jacketed) consisted of a tube with an internal diameter of 5 mm and a length of 2.05 m, which was filled with 19 g of the same catalyst.

The fixed bed catalyst installed in the main reactor and postreactor, comprising 50% by weight of NiO, 17% by weight of CuO, 30.5% by weight of $ZrO_2$, 1.5% by weight of $MoO_3$ and 1% by weight of graphite, was activated by the following method. The reactors were heated to 180° C. under ambient pressure with 42 l (STP)/h of nitrogen and 1.2 l (STP)/h of hydrogen, and kept under these conditions for 19 h. The hydrogen was increased from 1.2 to 6.5 l (STP)/h, and the reactor was kept at a temperature of 180° C. for a further 7.5 h. The nitrogen feed was turned off and the activation was continued with 6.5 l (STP)/h of hydrogen at 180° C. for 12 h. Subsequently, the hydrogen feed was turned off and the nitrogen feed was adjusted to 6 l (STP)/h. The reactors were cooled to a temperature of 60° C. The hydrogen feed was reduced to 1.6 l (STP)/h and the isopulegol feed was commenced.

By means of a centrifugal pump, a circulation was pumped through the main reactor at a rate of about 500 g/h at a feed of L-isopulegol of 24.5 g/h (total amount 588 g) with a purity of 99.9% by weight and 99.8% ee. The hydrogen pressure was kept constant at 40 bar. The main reactor was operated at a temperature of 85° C. and the postreactor at 75° C. All pipelines were provided with electrical trace heating to prevent the crystallization of the enantiomerically pure L-menthol (m.p. 44° C.). This afforded L-menthol in an amount of 597 g, corresponding to a rate of 24.9 g/h. The L-menthol thus obtained (99.8% ee) was analyzed by gas chromatography. The chemical purity of the L-menthol output is compiled in Table 1.

TABLE 1

| GC analysis of the L-menthol output (GC area %) | | | | | |
|---|---|---|---|---|---|
| Menthone/ isomenthone | L-menthol | Neomenthol | Neoisomenthol | Isomenthol | L-isopulegol |
| 0 | 99.6 | 0.19 | 0 | 0 | 0.19 |

Example 2

Example 1 was repeated using L-isopulegol with a purity of 99.9% by weight and 99.8% ee, which was introduced at a rate of 12.6 g/h (total amount 303 g) into the reactor at a hydrogen pressure of 40 bar. The main reactor (MR) was heated to 80° C., the postreactor to 75° C. L-menthol (99.8% ee) was obtained in an amount of 306 g corresponding to a rate of 12.8 g/h. The chemical purity of the L-menthol output is compiled in Table 2.

TABLE 2

| GC analysis of the L-menthol output (GC area %) | | | | | |
| --- | --- | --- | --- | --- | --- |
| Menthone/isomenthone | L-menthol | Neomenthol | Neoisomenthol | Isomenthol | L-isopulegol |
| 0 | 99.7 | 0.25 | 0 | 0 | 0 |

Example 3

Example 1 was repeated using L-isopulegol with a purity of 97.1% and 84% ee, which was introduced at a rate of 24.5 g/h (total amount 466 g) into the reactor at a hydrogen pressure of 40 bar. The main reactor (MR) was heated to 80° C., the postreactor to 70° C. The L-isopulegol used had the following composition: L-isopulegol: 97.1 GC % by weight, citronellol: 0.05 GC % by weight, citronellal: 0.40 GC % by weight, isopulegol isomer: 0.45 GC % by weight, secondary components: 0.34 GC % by weight. L-menthol (84% ee) was obtained in an amount of 468 g, corresponding to a rate of 24.6 g/h. The chemical purity of the L-menthol output is shown in Table 3.

By means of a centrifugal pump, a circulation was conducted through the main reactor at a rate of about 500 g/h at a feed of L-isopulegol of 24.5 g/h (total amount 588 g) with a purity of 99.8% and 99.8% ee at a constant hydrogen pressure of 30 bar. The main reactor was operated at a temperature of 50° C. and the postreactor at 60° C. All pipelines were provided with electrical trace heating to prevent crystallization of the enantiomerically pure L-menthol (m.p. 44° C.). L-menthol (99.8% ee) was obtained in an amount of 597 g, corresponding to a rate of 24.9 g/h. The product thus obtained was analyzed by gas chromatography. The results are compiled in Table 4.

TABLE 3

| GC analysis of the L-menthol output (GC area %) | | | | | | |
| --- | --- | --- | --- | --- | --- | --- |
| Menthone/isomenthone | L-menthol | Neomenthol | Neoisomenthol | Isomenthol | L-isopulegol | Secondary comp. |
| 0.08/0 | 97.3 | 1.0 | 0.29 | 0.20 | 0.29 | 0.33 |

TABLE 4

| GC analysis of the resulting L-menthol (GC area %) | | | | | | |
| --- | --- | --- | --- | --- | --- | --- |
| Menthone/isomenthone | L-menthol | Neomenthol | Neoisomenthol | Isomenthol | L-isopulegol | Secondary comp. |
| 0.64/0.56 | 97.5 | 0 | 0.66 | 0 | 0.29 | 0.10 |

Comparative Example 1

A hydrogenation apparatus consisting of a main reactor (MR) and a postreactor (PR) was used. The main reactor had 5 tubes, connected in series, with an internal diameter of 5 mm and a length of 1.3 m, which were filled with 104 g (127 ml) of a fixed bed catalyst consisting of 0.47% by weight of palladium on a γ-Al$_2$O$_3$ support in the form of extrudates of length 4 mm. The postreactor (jacketed) consisted of a tube with an internal diameter of 5 mm and a length of 1.9 m, which was filled with 27 g (35 ml) of the same catalyst.

The invention claimed is:

1. A process for preparing racemic or optically active menthol of the formula (I)

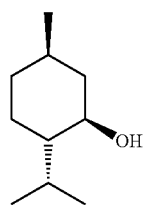

(I)

by catalytically hydrogenating racemic or optically active isopulegol of the formula (II)

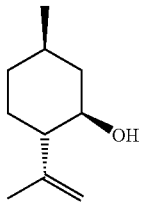

in the presence of hydrogen and a catalyst comprising
   from 30 to 70% by weight of oxygen compounds of nickel, calculated as NiO,
   from 15 to 45% by weight of oxygen compounds of zirconium, calculated as $ZrO_2$,
   from 5 to 30% by weight of oxygen compounds of copper, calculated as CuO and
   from 0.1 to 10% by weight of oxygen compounds of molybdenum, calculated as $MoO_3$,
where the figures in % by weight are based on the dry unreduced catalyst.

2. The process according to claim 1 for preparing L-menthol proceeding from L-isopulegol.

3. The process according to claim 1, wherein a catalyst comprising
   from 45 to 55% by weight of oxygen compounds of nickel, calculated as NiO,
   from 25 to 35% by weight of oxygen compounds of zirconium, calculated as $ZrO_2$,
   from 5 to 20% by weight of oxygen compounds of copper, calculated as CuO,
   from 1 to 3% by weight of oxygen compounds of molybdenum, calculated as $MoO_3$ and
   from 0 to 5% by weight of further components,
is used, where the figures in % by weight add up to 100% by weight and are based on the dry unreduced catalyst.

4. The process according to claim 1, wherein the catalyst is used in the form of an unsupported catalyst.

5. The process according to claim 1, wherein the catalyst is used in the form of a fixed bed catalyst.

6. The process according to claim 1, wherein menthol of the formula (I) is obtained in a purity of at least 99% by weight.

7. The process according to claim 1, wherein isopulegol of the formula (II) is used in a purity of at least 99% by weight.

8. The process according to claim 1, wherein the hydrogenation is performed at a hydrogen pressure in the range from 5 to 200 bar absolute.

9. The process according to claim 1, wherein the hydrogenation is performed at a temperature in the range from 50 to 130° C.

10. The process according to claim 1, wherein the hydrogenation is performed stepwise in a cascade of reactors.

11. The process according to claim 1, wherein the hydrogenation is performed continuously.

12. The process according to claim 1, which is performed without addition of solvents.

13. The process according to claim 1, wherein the catalyst hourly space velocity is from 0.1 to 1.0 kg of isopulegol per kg of catalyst and per hour.

* * * * *